United States Patent [19]

Deming et al.

[11] Patent Number: 5,354,742
[45] Date of Patent: * Oct. 11, 1994

[54] WATER-DISPERSIBLE GRANULES AND PROCESS FOR THE PREPARATION THEREOF

[75] Inventors: John M. Deming, Hazelwood; John M. Surgant, Sr., Ladue, both of Mo.

[73] Assignee: Monsanto Company, St. Louis, Mo.

[*] Notice: The portion of the term of this patent subsequent to Jun. 26, 2007 has been disclaimed.

[21] Appl. No.: 257,561

[22] Filed: Oct. 14, 1988

Related U.S. Application Data

[63] Continuation of Ser. No. 883,684, Jul. 9, 1986, abandoned.

[51] Int. Cl.$^5$ ............... A01N 57/00; A01N 37/18; C07C 223/00
[52] U.S. Cl. .................... 514/117; 514/210; 514/216; 514/287; 514/339; 514/423; 514/521; 514/616; 514/618; 514/619; 504/100; 504/116; 504/133; 504/134; 504/279; 504/234; 504/266; 546/21; 548/111; 564/152; 564/154; 564/155
[58] Field of Search ............... 71/118, DIG. 1; 504/133, 116, 100, 134, 229, 234, 256; 514/117, 287, 616, 216, 339, 423, 521, 618, 619, 210; 548/111; 546/21; 564/152, 154, 155

[56] References Cited

U.S. PATENT DOCUMENTS

| | | | |
|---|---|---|---|
| 3,429,827 | 2/1969 | Ruus | 424/469 |
| 3,577,515 | 5/1971 | Vandegaer | 422/22 |
| 3,737,337 | 6/1973 | Schmoring et al. | 252/319 |
| 3,920,442 | 11/1975 | Albert et al. | 71/DIG. 1 |
| 4,157,983 | 6/1979 | Golden | 252/319 |
| 4,235,872 | 11/1980 | Tocker | 427/213.34 |
| 4,244,836 | 1/1981 | Frensch et al. | 252/316 |
| 4,280,833 | 7/1981 | Beestman et al. | 71/DIG. 1 |
| 4,557,755 | 12/1985 | Takahashi et al. | 71/118 |

FOREIGN PATENT DOCUMENTS

| | | | |
|---|---|---|---|
| 0165227 | 12/1985 | European Pat. Off. | 71/118 |
| 6707830 | 12/1968 | Netherlands | 71/DIG. 1 |
| 2042892 | 10/1980 | United Kingdom . | |

*Primary Examiner*—C. Warren Ivy
*Assistant Examiner*—Raymond Covington
*Attorney, Agent, or Firm*—Gordon F. Sieckmann; Stanley M. Tarter; Richard H. Shear

[57] ABSTRACT

The invention is directed to a pesticide composition comprising free flowing, essentially spherical, water-dispersible granules wherein said water-dispersible granules are from about 150 to about 850 microns in diameter; wherein said granules contain up to about 8.0% by weight moisture; wherein each individual water-dispersible granule is an aggregation of individual spherical microcapsules which contain at least one water-insoluble pesticide within a polymeric shell wall; and wherein said water-dispersible granule disintegrates upon contact with water to release said individual microcapsules.

The invention also relates to dry flowable pesticidal formulations of the above water-dispersible granules, together with formulation adjuvants.

The invention is further directed to a process for preparing a water-dispersible granule by spary drying an aqueous suspension comprising discrete microcapsules containing at least one water-insoluble pesticide within a polymeric shell wall suspended in an aqueous liquid.

34 Claims, No Drawings

WATER-DISPERSIBLE GRANULES AND PROCESS FOR THE PREPARATION THEREOF

This is a continuation of application Ser. No. 883,684, filed Jul. 9, 1986 now abandoned.

BACKGROUND OF THE INVENTION

This invention relates to a process of preparing water-dispersible granules and to water-dispersible granules produced by said process. The water-dispersible granules of the invention are formed by aggregating small microcapsules, which contain one or more water-insoluble pesticides within a polymeric shell wall, into larger spherical granules.

For some low melting solids/liquids, micro-encapsulation offers the only means of maintaining stable sprayable suspensions of that chemical in water. Having accomplished a stable suspension, microencapsulated pesticide formulations which are aqueous suspensions of microcapsules offer many desirable features. In some cases, reduced toxicity and extended activity of the encapsulated pesticide has been noted. Many pesticides decompose or volatilize quickly, thus reducing the effectiveness of the material; microencapsulation of such materials can postpone the decomposition of the pesticide. Micro-encapsulation of pesticidal materials can also enhance the safety of the pesticide for the applicator. Since the pesticide is enclosed in a polymeric shell wall the applicator is not directly exposed to the chemical. Another advantage of encapsulation of an active pesticidal agent lies in the possibility of a combination of substances that cannot be blended or are incompatible with one another, e.g., water-insoluble pesticides with water-soluble pesticides or water soluble fertilizers.

For liquid products, microencapsulation can eliminate the cost, availability, flamability, toxicology disadvantages of solvents by permitting water to be used as the suspending medium. For solid formulations derived from solutions or suspensions, those advantages generally pertain to the process as well as to the end use of the product.

Various methods are known in the art for microencapsulation of water-insoluble pesticides via interfacial polymerization reaction. U.S. Pat. Nos. 4,360,376, 3,429,827, 3,577,515 and 4,280,833 provide a good summary of the methods which are available. U.S. Pat. No. 4,280,833 describes the microencapsulation of concentrated amounts of water-insoluble pesticide materials on the order of 480-700 grams per liter, this previously unattainable high concentration offers a distinct energy saving advantage when water driveoff is required to convert the liquid to a solid.

While it can be advantageous to encapsulate pesticidal materials, it is also advantageous to have the pesticidal material in dry form. Dry pesticide formulations can be stored for long periods of time, over wide extremes of temperature, without destroying the stability of the formulation. It is easier and less expensive to dispose of containers in which dry pesticidal materials are stored since these are most often made of paper, which can be safely burned if the solid empties completely from the bag leaving no residue. Still more preferable is the use of water-soluble plastic bags in which to store, ship and add to water the water-dispersible granules or other dry-form pesticides. Shipping costs can be reduced since the solvent or water carrier of emulsifiable concentrate and water-based flowable pesticide formulations is eliminated. The most common types of dry pesticide formulations are wettable powder and granule formulations. The preparation of each type of formulation is known.

Various methods are described in the technical end patent literature for producing various forms of encapsulated products for pesticidal materials. Typically, the encapsulated product may be in the form of microcapsules of encapsulated material suspended in a carrier (continuous) medium or in the form of dried microcapsules, powders, grannulates, microgrannulates or water-dispersible granules. Examples of the foregoing products may be found in British Patent No. 2,042,892 and in the following U.S. Pat. Nos. 3,429,827, 4,244,836, 4,309,213, 3,737,337, 4,157,983, 4,235,872, and 3,577,515.

Other forms of water-dispersible, non-encapsulated products are described in U.S. Pat. Nos. 3,657,446, 3,639,617, 3,954,439, 2,870,059, 3,920,442, 4,511,395, 4,134,725, 4,183,740 and 3,854,981, in German Patent No. DT-1,642,122 and So. African Application No. 692053. The products produced in the above exemplified patents may be dried typically in an air flow, by evaporation, by spray drying, etc.

Yet another common form of pesticidal product mentioned above is the wettable powder, as exemplified in British Patent No. 2,037,585 and U.S. Pat. Nos. 3,791,811 and 3,731,551.

The most common wettable powder pesticide formulation is one in which fine particles of a high melting solid, crystaline pesticide are combined with a finely-divided solid carrier, e.g., silicates or alumino silicates comprising single lattice or double lattice clays. The surface active agents allow the concentrate to be diluted in water to field strength to form stable, sprayable suspensions. Most high melting solid pesticides can be processed as a wettable powder in the 60-90% concentration range; the main requirement being that they exhibit appropriate chemical compatibility with the finely divided, solid carrier. In order for low melting actives to be formulated as wettable powders they must first be absorbed into highly porous media such as diatomaeous earth, pearlite or manufactured silicas to a degree that the mixture exhibits the properties of a solid. This dilution essentially reduces wettable powder concentrations of liquids to less than 60%, with 40-50% a more common range. Further, low melting actives which undergo a phase change at ambient storage temperatures (e.g., −1020 to +50° C.) usually present such a caking problem from crystal formation and growth that the use of an absorbing agent is futile and cake-free solid formulations having concentrations of >20% are impossible to attain. Alachlor and trillate are excellent examples of such chemicals.

The primary disadvantage of wettable powder pesticide formulations is that they tend to be dusty, posing health problems to the applicator if the pesticide material is irritating or toxic and handling problems during the preparation of the material. Further, wettable powders tend to have low bulk density and, thus, do not wet up rapidly when added to water. Inability to wet up can result in excessive mixing times and/or the formation of "lumps" of wettable powder in the water. These lumps are difficult to disperse in the water making it difficult to get even distribution of the pesticide throughout the water and, thus, even application of the pesticide when applied. In extreme cases, lumping can result in clogging of sprayer nozzles.

A granular pesticide formulation is one which usually involves impregnation of molten pesticidal agent into the pores of a preformed granule, but may involve agglomeration of high melting solids with powdered inerts such as clay. For impregnation, the active ingredient must be a liquid at a temperature below about 120° C. or be compatible with a liquid carrier which can take solubilized or suspended active ingredients into the pores of the granule during a liquid-solid blending operation. Common granule carriers are clays, attapulgite, bentonite, sepiolite and the like.

Granular pesticides comprising high-melting solids may also be formed by extrusion, agglomeration or core coating.

A disadvantage of some conventional granule pesticide formulations is that the total amount of active pesticide carried on the granule is limited by carrier, equipment metering and efficacy considerations to 5–25% loadings. These low loadings contribute to the expense of the granules. This, and the added expense of separate granular application equipment, are economic limitations on granule use. Caking can be a problem if the active pesticidal agent readily migrates to the surface of the granule making it "sticky". Finally, since many granules are irregularly shaped, some dusting occurs as the granules wear against each other in the package during storage and handling.

Although, as indicated above, water-dispersible granules are generally known and have been commercially available for sometime now, the present invention affords an economical means of making water-dispersible granules from chemicals and combinations thereof having a wide range of melting points, including low melters. The process according to this invention permits the formation of granules having a particularly advantageous structure and physical properties and formulation compatible with that process.

As will be described in more detail herein, an important portion of the water-dispersible granule of the invention is an aggregate of many small polymeric microcapsules containing a water-insoluble pesticide. The geometry and composition of the water-dispersible granules of the invention permit them to be free flowing and relatively dust-free. Since the active pesticidal agent is encapsulated, the water-dispersible granules of the invention pose very little hazard to the user when handled. Another advantage of microencapsulated water-dispersible granules is the ability to produce a product package containing a plurality of pesticides wherein antagonistic action between the pesticides is reduced or eliminated by means of the capsule shell.

The water-dispersible granules of the invention have bulk densities sufficiently high to readily wet-up when added to the water in a farmer's spray tank thus eliminating the wetting or lumping problem of wettable powders.

The water-dispersible granules of the invention immediately reconstitute when added to water; by that it is meant that the large aggregates dissociate or break apart into the tiny, individual microcapsules which disperse to their original pre-agglomerated form throughout the water. Since the pesticide is encapsulated, one can get a high degree of loading of the active, on the order of 65–90% active pesticidal agent for water-dispersible granule as contrasted to the maximum 50% loading attainable with commercially available granules. Further, one is able to add the encapsulated pesticide to aqueous solutions, e.g., liquid fertilizer solutions which might ordinarily be antagonistic to the unencapsulated pesticide.

SUMMARY OF THE INVENTION

In one embodiment, the present invention relates to a pesticidal composition comprising water-dispersible granules and formulations thereof. The granules of the invention are essentially spherical, aggregates of discrete microcapsules containing water-insoluble pesticides. As a collective mass, The granules are free-flowing, relatively dust free, non-caking and disperse immediately in aqueous media.

The water-dispersible granules of the invention comprise an aggregation of a plurality of individual essentially spherical microcapsules of one or more water-insoluble pesticides encapsulated within a polymeric shell wall, formulation adjuvants and no more than about 8% by weight water. Upon contact with an aqueous medium, the granules disintegrate to release the individual microcapsules which disperse uniformly throughout said aqueous medium.

The optimum particle size distribution of the water-dispersible granules should be such that from about 90–95% of the granules have diameters within the range of about 180–420 microns, although larger particle-size granules, up to about 850 microns will function satisfactorily; however, these larger particles reconstitute more slowly. Aggregates less than about 150 microns will tend to result in wind drift, dry flowability and wetting problems. Typical particle size distribution for the granules herein is as follows:

| | |
|---|---|
| 70–75% | will pass through 40 mesh and be retained on 60 mesh screen (U.S. Standard Sieve Series), i.e., 40/60 sieve screens; 420–250 microns; |
| 20–15% | on 60/80 sieves; 250–180 microns; |
| 8–9% | on 80/100 sieves; 180–150 microns; |
| 2–1% | less than 150 microns. |

The moisture content of the water-dispersible granules herein should be within the range of about 0.1–8 percent maximum and, preferably, no more than 4% moisture and still more preferably, within the range of 1–2 weight percent.

The water-dispersible granules of this invention should have a suitable bulk density within the range of about 23–96 kg/m$^3$ preferably about 48–96 kg/m$^3$, with about 56–72 kg/m$^3$ being an optimum bulk density.

A further embodiment of the invention relates to formulations of the above-described aggregates of water-dispersible granules together with necessary formulation adjuvants, including emulsifier, binders, dispersants, separators, detackifiers, etc., which create a separating and bridging connection between the microcapsules within said granules and between the aggregated granules themselves to aid in preventing fusion, caking and attrition therebetween and caking of the dry aggregate mass during storage. Of the various formulation adjuvants, it is most important that an inorganic salt, e.g., a chloride, nitrate or sulfate of ammonium or of an alkali metal or alkaline earth metal, such as sodium, potassium or calcium, zinc, copper, manganese or magnesium be present as a binder/dispersant to aid in reconstitution of the aggregates when mixed with water.

Rapid removal of water in the spray-drying process minimizes component migration and, therefore, maintains the homogeneous distribution of separating aids between the microparticles.

The formulations of this invention comprise one or more pesticides, e.g., herbicides, fungicides, insecticides, etc., encapsulated within the microcapsules forming the water-dispersible granules. The concentration of the pesticide should be at least sufficient to be pesticidally effective and range upwardly to about 90% by weight of said granules. A suitable concentration range is 0.1–90%, and, typically, from about 5–80% by weight. Additional embodiments include the encapsulation of safeners or antidotes for herbicides together with the herbicides within the same shell wall.

A further embodiment of the invention relates to a process for preparing the above-described water-dispersible granule which comprises:

(a) forming an aqueous suspension comprising at least one water-insoluble pesticide encapsulated within a polymeric shell wall suspended in an aqueous liquid; and (b) forming droplets of said aqueous suspension and spray drying said droplets to form a water-dispersible granules of structure and composition described above.

DETAILED DESCRIPTION OF THE INVENTION

In a primary aspect, the invention is directed to a pesticidal composition of water-dispersible granules as described above.

As also noted above, another aspect of the invention relates to formulations comprising aggregates of said granules and formulation adjuvants.

The invention is further directed to a process for preparing water-dispersible granules and formulations comprising:

(a) forming an aqueous suspension comprising microcapsules containing at least one water-insoluble pesticide within a shell wall of polymeric material suspended in an aqueous liquid; and (b) forming droplets of said aqueous suspension and spray drying said droplets to form water-dispersible granules having the structure and composition described above.

The term "aggregate" as used herein refers to the collection or aggregation of individual, small spherical microcapsules into a larger, generally spherical particle which is referred to herein as a water-dispersible granule. When the dry, free-flowing water-dispersible granules (aggregates) of the invention are added to water, they disassociate back to the individual spherical microcapsules containing the water-insoluble pesticide. These microcapsules disperse throughout the water forming an aqueous suspension; i.e., solids dispersed throughout an aqueous liquid.

As used herein the term "dry" or "dry-flowable" refers water-dispersible granules having a moisture content of no greater than 8% by weight.

By "free-flowing" is meant that the water-dispersible granules are essentially free of caking or fusing of the granules and are freely pourable, as from one container to another.

The dry, free-flowing water-dispersible granules of the invention are prepared by spray drying an aqueous suspension comprising microcapsules containing one or more water-insoluble pesticides within a polymeric shell wall. Droplets of said aqueous suspension, each containing many microcapsules are spray dried. As the water is removed from each droplet, an essentially spherical "aggregate", referred to herein as a water-dispersible granule, is formed.

As used herein, the term "aqueous suspension" refers to a two-phase system in which solid particles, i.e., small, spherical microcapsules containing a water-insoluble pesticide(s), are suspended in an aqueous (continuous) phase liquid. The aqueous suspension may contain, in addition to the microcapsules and the emulsifier which was used in the process of microencapsulation, small amounts of other water-soluble materials, e.g., salts, emulsifiers, dispersants, lower alkylene glycol, etc. and finely divided solids, e.g., clays and silicas. Such materials are described in greater detail hereinafter.

The small, individual microcapsules remain discrete, individual, spherical particles which are separated from and bridged to each other by a thin layer of salts and emulsifier which is left behind when water is rapidly removed from the aqueous suspension.

It is, thus, an advantage of the spray drying process used to make the aggregates herein that the separation aids are kept from migrating from their desired locations between the granules. The more important separation aids appear to be inorganic salts such as NaCl, KCl, $CaCl_2$ and $(NH_4)_2SO_4$ and a minimum amount of water of hydration. Other separation means include surfactants, water-soluble polymers, higher alcohols and other water-soluble or dispersed components. Still other means to maintain good separation include maintenance of spray-drying temperatures below the fusion temperature of the granule shell. This may be done by a combination of the temperature and product moisture content at the spray tower exit and product feed mode. For example, using the counter-current feed mode, at a moisture content of 1–3 weight %, the exit temperature should be within the range of about 122°–149° C. or at 8–10% moisture, the temperature can be within the range of about 93°–121° C.

There are several techniques known for microencapsulating pesticide materials; see for example MICROENCAPSULATION PROCESSES AND APPLICATIONS edited by Jan E. Vandegaer, 1974 Plenum Press, New York and London. Such processes include coacervation encapsulation, interfacial condensation polymerization, and fluid bed coating. The preferred method for use herein is interfacial polycondensation microencapsulation and especially the process described by U.S. Pat. No. 4,280,833 as well as Serial No. 619,752 filed Jun. 12, 1984, Ser. No. 655,827 filed Oct. 1, 1984, and Ser. No. 566,108 filed Dec. 27, 1983, all of which describe encapsulation of concentrated amounts of water-insoluble pesticides, i.e., greater than 480 grams of water-insoluble material per liter of total composition. High concentration microencapsulation is achieved by use of specific emulsifiers and these higher starting concentrations are of both energy and process benefit in accomplishing a dry product.

Briefly, microencapsulation via interfacial condensation polymerization reaction involves encapsulating a water-immiscible material within a shell wall of polycondensate, e.g., polyurea, polyamide, polysulfonamide, polyester, polycarbonate, or polyurethane by (1) providing an aqueous solution containing an emulsifier capable of forming a stable oil-in-water emulsion when concentrated amounts of discontinuous phase liquid are present vis-a-vis the continuous or aqueous phase liquid; (2) forming an organic or discontinuous phase liquid which consists essentially of the water-insoluble pesticide (the material to be encapsulated) with a first shell wall monomer dissolved therein; (3) addition of the discontinuous liquid to the aqueous phase,-with agitation, to form a dispersion of small droplets discontinuous phase liquid throughout the aqueous phase i.e., an oil-in-water emulsion is formed); (4) addition of a second water-miscible shell wall monomer, with continued agitation, to the oil-in-water emulsion; and (5) reaction of the second shell wall monomer with the first shell wall monomer to form a polymeric shell wall about the water-insoluble pesticide.

At the completion of the encapsulation reaction there is an aqueous suspension which is a two-phase system wherein solid particles (microcapsules) are suspended in an aqueous (continuous) phase liquid. In addition to the solid particles, the aqueous liquid contains the emulsifier which was used in the encapsulation process. Additionally, various other materials may be added to the aqueous suspension which aid in spray drying or which aid in the disassociation of the water-dispersible granule when it is added to water, or, improves the non-caking, non-dusting, strength or flow characteristics of the granule in its spray-dried form. Such materials are hereinafter referred to as "suspension adjuvants", or when applied to the spray-dried granule as "agglomeration adjuvants".

As used herein the term "suspension adjuvant" refers to any material which is added to the aqueous suspension and which subsequently facilitates drying of the droplet of aqueous suspension during the spray dry process or which facilitates the disassociation of the water-dispersible granule when it is added to water or improves the dry strength and other characteristics of the granule. The suspension and agglomeration adjuvants useful herein are water-soluble salts, e.g., $(NH_4)_2SO_4$, NaCl, $CaCl_2$, water-soluble emulsifiers, or polymers e.g., polyvinyl pyrrolidone (PVP), polyvinyl alcohol (PVA) electrolytes, natural gums, or other additives, such as water-soluble alkylene-glycols, finely divided solid particles, e.g., clays and silicas.

The water-insoluble pesticide(s) which is the active agent of the water-dispersible granule of the invention and which is encapsulated is suitably any liquid, oil., meltable solid or solvent-soluble pesticide, into which the first shell wall monomer can be dissolved and which is nonreactive thereto. Such water-immiscible pesticides include as representative herbicides, e.g., α-chloro-2',6'-diethyl-N-methoxymethyl acetanilide (commonly known as alachlor), N-butoxymethyl-α-chloro-2',6'-diethylacetanilide (commonly known as butachlor), 2'-methyl-6'-ethyl-N-(1-methoxy-prop-2-yl)-2-chloroacetanilide (commonly known as metolachlor), 2'-t-Butyl-2-chloro-N-methoxymethyl-6'-methylacetanilide, α-chloro-N-(2-methoxy-6-methylphenyl)-N-(1-methylethoxymethyl)acetamide, α-Chloro-N-(ethoxymethyl)-N-[2-methyl-6-(trifluoromethyl)phenyl]-acetamide, α-chloro-N-methyl-N-[2-methyl-6-(3-methylbutoxy) phenyl]acetamide, α-Chloro-N-methyl-N-(2-methyl-6-propoxyphenyl)acetamide, N-(2-butoxy-6-methylphenyl)-α-chloro-N-methyl acetamide, isobutyl ester of (2,4-dichlorophenoxy)acetic acid, 2-chloro-N-(ethoxymethyl)-6'-ethyl-o-acetotoluidide (commonly known as acetochlor), 1-(1-cyclohexen-1-yl)-3-(2- fluorophenyl)-1-methyl urea, S-2,3,3-trichloro-allyl-diisopropyl thiocarbamate (commonly known as triallate), S-2,3-dichloroallyldiisopropylthiocarbamate (commonly known as diallate), α,α,α-trifluoro-2, 6-dinitro-N,N-dipropyl-p-toluidine (commonly known as trifluralin).

Certain high-melting herbicides, e.g., N-(3,4-dichlorophenyl)-N'-methoxy-N'-methylurea (commonly known as linuron) 4-amino-6-tert-butyl-3-(methylthio-as-triazine-5-(4H)one(common name metribuzin), cannot be encapsulated directly, but must first be solubilized by the water-insoluble co-herbicide and the mixture then encapsulated.

Representative safeners (antidotes) for use with herbicides which are specifically contemplated as being suitable for use in the water-dispersible granules of this invention include, e.g., 5-thiazolecarboxylic acid, 2-chloro-4-(trifluoromethyl),(phenylmethyl) ester, (common name "flurazole"), N-α,α-dichloroacetyl-1-oxa-4-azaspiro [4,5] decane (common name "AD-67"), N-α,α-dichloroacetyl-N,N-diallyl acetamide, N-α,α-dichloroacetyl-2,2-dimethyl-1,3-oxazolidine, N-α, α-dichloroacetyl-2,2,2-trimethyl-1,3-oxazolidine, α-[(cyanomethoxy) -imino]benzenacetonitrile, α-[(1,3-dioxypyran-2-yl-methoxy)-imino] benzenacetonitrile and the like.

The encapsulated herbicide may also include insecticides and/or fungicides as co-pesticide. However, the latter pesticides can only be those sufficiently low melting to be encapsulable, preferably below about 50° C., but operably plus or minus some 10°–15° C., i.e., 40°–65° C., either by themselves or in combination with the co-pesticide(s). Representative insecticides include, e.g., malathion, bromophos, methyl- and ethyl parathion, diazinon, etc. Representative low-melting fungicides include, e.g., buperimate, dinocat, edifenphos, Terrizole, Dowside-A and pyrazophos.

The encapsulated water-insoluble pesticide need not consist of only one type, but may be a combination of two or more various types of water-insoluble pesticides; e.g., such a combination may be one active herbicide with another active herbicide or an active herbicide or any other type of biocide or growth regulator, safener and/or an active insecticide. Higher melting solids need be solubilized within a second liquid active ingredient in order to be microencapsulated. Microencapsulation of higher melting solids is restricted more by the solubility of the solid in the liquid at encapsulation temperatures.

In the interfacial condensation encapsulation process used herein, the water-insoluble pesticide containing the first shell wall monomer dissolved therein comprises the organic or discontinuous phase liquid. The water-immiscible pesticide acts as the solvent for the first shell wall monomer thus avoiding the use of other water-immiscible organic solvents and allowing for a concentrated amount of water-insoluble pesticide in the final encapsulated product. The water-insoluble pesticide and first shell wall component are pre-mixed to obtain a homogeneous discontinuous phase liquid before addition to, and emulsification in, the aqueous phase to form the oil-in-water emulsion.

The concentration of water-insoluble pesticide initially present in the discontinuous phase liquid should be sufficient to provide at least about 300 grams of water-insoluble pesticide per liter of aqueous suspension. However, this is by no means limiting and a greater amount can be used. In practical operation, as will be recognized by those skilled in the art, the use of extremely high concentrations of water-insoluble pesticide will result in very thick suspensions of microcapsules. In general, the concentration of water-insoluble pesticide will range from about 400 grams to about 700 grams per liter of aqueous suspension. The preferred range is from about 480 grams to about 600 grams per liter of aqueous suspension.

The term "first shell wall monomer" refers to a material or mixture of materials which is soluble in the material to be encapsulated and which is capable of reacting with the second shell wall monomer to form a polymeric shell wall about the material to be encapsulated. As previously stated, the material to encapsulated together with the first shell wall monomer constitute the discontinuous or organic phase liquid.

The term "second shell wall monomer", as used herein, refers to a water soluble material, i.e., a material which is soluble in the aqueous phase liquid and which will react with the first shell wall monomer to form a polycondensate shell wall about the material to be encapsulated. Table 1 illustrates various types of polycondensate shell walls formed when various first and second shell wall monomers are utilized in the process of encapsulation described herein:

TABLE 1

| First Shell Wall Component | Second Shell Wall Component | Polymeric Shell Wall |
|---|---|---|
| Diacid or Polyacid Chlorides | Diamine or Polyamine | Polyamide |
| Dichloroformates or Polychloroformates | Diamine or Polyamine | Polyurethane |
| Diisocyanates Polyisocyanates | Diols or Polyols | Polyurethane |
| Disulfonyl or Polysulfonyl Chlorides | Diamine or Polyamine | Polysulfonamide |
| Diisocyanates or Polyisocyanate | Diamine or Polyamine | Polyurea |
| Diacid or Polyacid Chlorides | Diols or Polyols | Polyester |
| Dichloroformates or Polychloroformates | Diols or Polyols | Polycarbonate |

Examples of suitable difunctional, acid-derived shell wall monomers are sebacoyl chloride, ethylene bischloroformate, phosgene, terephthaloyl chloride, adipoyl chloride, azelaoyl chloride (azelaic acid chloride), dodecanedioic acid chloride, dimer acid chloride, and 1,3-benzenesulfonyl dichloride. Polyfunctional compounds of this type are exemplified by trimesoyl chloride, 1,2,4,5 benzene tetracid chloride, 1,3,5 benzene trisulfonyl chloride, trimer acid chloride, citric acid chloride, and 1,3,5 benzene trischloroformate. Intermediates similarly useful in the organic or discontinuous phase also include diisocyanates and polyisocyanates, for example, toluene diisocyanate, hexamethylene diisocyanate, methylene diphenylisocyanate and polymethylene polyphenylisocyanate. Preferred are the last-named polyisocyanates, represented by commercially-available polymethylene polyphenylisocyanates such as PAPI ® and PAPI-135 ® (registered trademarks of the Upjohn Company) and Mondur-MR ® (registered trademark of Mobay Chemical Company).

Examples of suitable diols for use as intermediates in the aqueous phase are bisphenol A [2,2 bis-(p,p'-dihydroxy diphenyl)propane], hydroquinone, resorcinol, catechol and various glycols such as ethylene glycol, pentanediol, hexanediol, dodecanediol, 1,4-butanediol and the like. Polyfunctional alcohols of this character, e.g., triols, are exemplified by pyrogallol (1,2,3-benzenetriol), phloroglucinol dihydrate, pentaerythritol, trimethylolpropane, 1,4,9, 10-tetrahydroxyanthracene, 3,4-dihydroxyanthranol, diresorcinol and tetrahydroxyquinone.

Instances of suitable diamines and polyamines, usually selected as water soluble per se or in-water soluble salt form, where such reactant is to be included in the aqueous phase, are polymethylene diamines, phenylene diamine, toluene diamine, diethylene triamine and piperazine. Amines which are effective as polyfunctional reactants, are, e.g., 1,3,5-benzene triamine trihydrochloride, 2,4,6-triamino toluene trihydrochloride, polyethylene imine, 1,3,6-triaminonaphthalene, 3,4,5-triamino-1,2,4-triazole, melamine, and 2,4,5,8-tetramino anthraquinone. Amines which have a functionality greater than 2 but less than 3 and which may provide a degree of cross-linking in the shell wall are polyalkylene polyamines, e.g., tetraethylene pentamine, pentaethylene hexamine, and the like. Particularly suitable amines are the polyfunctional amines which are capable of reacting with polymethylene polyphenylisocyanate to form a polyurea shell wall. The polyfunctional mines should be water soluble salt form. The usable polyfunctional amines can be selected from a wide range of such materials. Suitable examples of polyfunctional amines which may be used in this invention include, but are by no means limited to the following: ethylenediamine, propylenediamine, isopropylenediamine, hexamethylenediamine, toluenediamine, ethenediamine, triethylenetetraamine, tetraethylenepentamine, pentaethylenehexamine, diethylenetriamine, bix-hexamethylenetriamine and the like. The amines may be used alone or in combination with each other, preferably in combination with 1,6-hexamethylenediamine (HMDA). 1,6-hexamethylenediamine is preferred for use in the process of the present invention.

The first shell wall monomer and the second shell wall monomer form the shell wall which surrounds or encapsulates the water-insoluble pesticide. The shell wall content of the capsules may vary from about 5 percent to about 30 percent, preferably 6 to 20 percent and most preferably 7–10 percent by weight of the water-insoluble pesticide.

The amount of first shell wall monomer and second shell wall monomer to be used in the process is determined by the percent shell wall content produced. Generally, there will be present from about 3.5 percent to about 21.0 percent first shell wall monomer, and from about 1.5 percent to about 9.0 percent second shell wall monomer, relative to the weight of the water-insoluble pesticide present in the reaction.

In order to obtain encapsulation of from 400 to 700 grams per liter of water-immiscible pesticide it is necessary to use the specific emulsifiers described below to achieve a stable oil-in-water emulsion. The emulsifying agents, which are advantageously used in encapsulating concentrated amounts of water-insoluble pesticide are:

1. The water-soluble salts of lignin sulfonate, e.g., the sodium, potassium, magnesium, calcium or ammonium salts of lignin sulfonate. The sodium salt of lignin sulfonate is preferred for use herein. Any commercially available lignin sulfonate salt which does not contain added surfactant, may be conveniently employed herein. Commercially available lignin sulfonate emulsifiers which may be mentioned are: Treax ®, LTS, LTK and LTM, respectively, the potassium, magnesium and sodium salts of lignosulfonate (50% aqueous solutions), Scott Paper Co., Forest Chemical Products; Marasperse CR ® and Marasperse CBOS-3 ®, sodium lignosulfonate, and Marasperse C21 ®, calcium sulfonate, Reed Lignin Co., Polyfon O ®, Polyfon T ®, Reax 88B ®, Reax 85B ®, sodium salts of lignin sulfonate, Westvaco Polychemicals.

2. Sulfonated naphthalene-formaldehyde condensates having the formula:

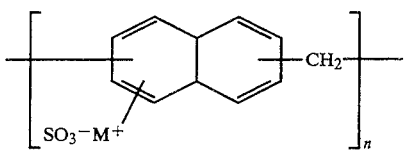

where n is 2 or 3 and M is an alkali or alkaline earth metal cation. Commercially available examples which may be mentioned are Tamol ® SN, the sodium salt of condensed naphthalene sulfonic acid manufactured by Rohm and Haas Company, Philadelphia, Pa. 19105; "Daxad" 11G, 16, 17 and 19, the sodium salt of polymerized alkyl naphthalene sulfonic acid, manufactured by W. R. Grace and Company, Organic Chemicals Division, Lexington, ME 02173;"Blancol" N, the sodium salt of sulfonated naphthalene-formaldehyde condensate manufactured by GAF Corporation, Chemical Products, 140 West 51st Street, New York, N.Y. 10020.

3. Sulfonated polystyrenes with molecular weights above about 1,000 and an equivalent weight per acid group between about 150 and about 750, as for example sulfonated polystyrenes of the formula:

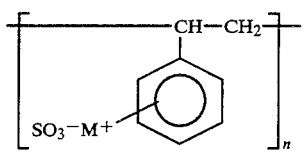

where n is greater than 5 and M is an alkali or alkaline earth metal cation. Commercially available examples of such materials are Versta ® TL 500 and TL 600, sulfonated polystyrene manufactured by National Starch and Chemical Corporation, 10 Findeine Avenue, Bridgewater, N.J. 08807.

4. Water-soluble alkylated polyvinylpyrrolidone (PVP) polymer; e.g., Ganex ® P-904 which has an average molecular weight of 16,000 and which is a 10% weight butylated-PVP polymer manufactured by GAF Corp., Chemical Products, 140 W. 51st St., New York, N.Y. 10020. U.S. Pat. No. 3,417,054 and 3,423,381 describe the preparation of such alkylated PVP polymers. Unalkylated PVP polymers which may be mixed with alkylated PVP polymers to produce a water-soluble PVP mixture which will form a stable oil-in-water emulsion under the process conditions described herein are Ganex ® K-15, K-30 and K-90 having average molecular weights of 10,000, 40,000 and 360,000 respectively; these materials are available from GAF Corporation.

The range of emulsifier concentration found most acceptable in the system will vary from about 0.5 percent to about 15 percent and preferably from about 2 percent to about 6 percent, based on the weight of the water-immiscible material and most preferably at from about 2.0 to about 4.0 percent and most preferably at a concentrate of 2 percent relative to the weight of the water-immiscible pesticide.

In the practice of the encapsulation process described herein, the temperature should be maintained above the melting point of the water-insoluble pesticide material but below the temperature wherein the discontinuous phase monomer will begin to hydrolyze or otherwise break down. For example, where it is desired to encapsulate a solid herbicide, it will be necessary to heat the herbicide to its molten state. Alachlor herbicide, for example, melts at 39.5° C. to 41.5° C. and the temperature of the process should accordingly be maintained in the 42°–45° C. range.

The agitation employed to establish the dispersion of discontinuous phase droplets in the aqueous phase may be supplied by any means capable of providing suitably high shear, that is, any variable shear mixing apparatus, e.g., a blender, a Brinkman Polytron homogenizer, Ross Model 100L homogenizer, Tekmar, and the like, can be usefully employed to provide the desired agitation.

The particle size of the microcapsules and other pesticide ingredients will range from about 1 micron up to about 100 microns in size. From about 1 to about 10 microns is an optimum range. From about 5 to about 50 microns is satisfactory for spray drying.

The aqueous suspension of microcapsules containing the water-insoluble pesticide and suspension and agglomeration adjuvants form the "feed stock" for subsequent spray drying. Droplets of feed stock are spray dried in a spray dry tower to produce the water-dispersible granules of the invention. The droplets are formed using conventional spray dry nozzles. The nozzle has two primary functions:

1. To atomize or break up the aqueous suspension into droplets of the desired size, and
2. To distribute these droplets in a specific pattern in the tower.

An appropriate nozzle is used to atomize the aqueous suspension in a spray drying tower where drying occurs. Generally, single-fluid hollow-cone nozzles of the type previously described are preferred as they produce large uniform droplets. As water is removed from each droplet an aggregate is formed consisting essentially of many small microcapsules associated together, with a fine layer of suspension adjuvant homogeneously interspersed between each microcapsule. The entire drying process may occur in the spray dry tower; however, to avoid the possibility of overheating of the aggregate which will result in the formation of a water-dispersible granule which will not dissociate when added to water; secondary drying may advantageously be used in the final stage.

Secondary drying is most advantageously accomplished by use of a vibra-fluidized bed for second stage drying. The water-dispersible granule product is dried in the spray dry tower, typically, to a moisture level of about 6% to about 10% by weight. It is sometimes possible to achieve moisture levels of about 2% or less in the spray tower itself. The granules are collected from the tower and passed through fluid-bed dryers to bring the moisture level of the water-dispersible granules to no more than 8.0% by weight and, preferably, about 4% and still more preferably about 1.0% to about 2.0% by weight.

In order to produce a water-dispersible granule having the particle size range described herein, it is necessary to produce as large and uniform a droplet as possible from a given nozzle orifice. The nozzle should be chosen so as to produce large uniform particles over a narrow distribution range. Larger droplets can be expected as the orifice size is increased at a given pressure. In general, lower pressure and higher feed-stock viscosity will increase particle size. In general, from 1379–2758×10³ N/m² will be required to produce the large uniform droplets; from 1379–2069×10³ N/m² may be used with about 1379×10³ N/m² found to be optimal for liquids in the 800–1200×10⁻³ N s/m² viscosity range often encountered for feedstocks described herein.

Multiple nozzles can be used to atomize the droplets of aqueous suspension into the spray tower. However, as will be recognized by one skilled in the art, the number of nozzles used will be limited by the drying capacity attainable in the tower.

Spray-dry nozzles found to be useful herein are single fluid, hollow-cone nozzles. A single-fluid, solid-cone nozzle may also be used herein and this nozzle is similar in design to the swirl-chamber nozzle except that a special cone or axial jet fills the center of the conical pattern. The resulting full-volumetric coverage enhances rates of mass and heat transfer between the spray liquid and gas passing through the cone. The included spray angle ranges from 30°–120°.

The above and other types of atomization devices are known and are commercially available as are fan-spray nozzles and disk atomizers. However, preferred for use herein are the single fluid, hollow-cone nozzles previously described.

Single-fluid nozzles are preferred over two fluid atomizers which are pneumatically operated to provide small atomized particles at low pressure. Single-fluid nozzles are particularly useful for spraying high viscosity materials and for the formation of larger droplets which, when dried produce large aggregates. The larger volume and greater density of droplets formed from single-fluid nozzles results in greater momentum to carry them into the dispersing air flow allowing for more efficient drying in the spray tower. The droplets formed are homogeneous and produce a narrow aggregate size distribution particularly when hollow-cone nozzles are employed to direct the spray from the nozzle at radial velocities. Size uniformity is important in providing the best product performance compromise by avoiding dust from small particles while still providing particles small enough to rapidly disperse in water. Size uniformity is also important in the drying process to provide uniform drying of individual particles to assure their rapid reconstitution in water.

The best results relative to product rate and quality by use of a mixed-flow fountain spray (wherein product feed into spray tower is in a direction opposite to the drying air stream) are achieved using a spray nozzle which produces a spray angle of from about 46° to 60° at pressure of about 1379–1896 N/m². Such nozzles produce atomization and projection of the aqueous suspension far enough up into the spray drying chamber to take advantage of available drying capacity. Angles greater than about 60° "fan out" and do not project high enough into the tower to take advantage of the maximum resonance time and drying capacity of the tower. This usually causes "wetting" or wall buildup in the tower.

The spray dryer is a large, usually vertical, chamber through which a hot gas is blown, and into which the aqueous suspension is sprayed by a suitable nozzle atomizer to form droplets. All droplets must be dried until no longer sticky, before they strike the chamber wall; therefore, the largest drop produced by a given nozzle determines the size of the spray chamber, and chamber shape is fixed by spray pattern. A spray dryer may be cocurrent, countercurrent, or mixed flow. Counter-current tends to expose the driest particle to the hottest temperature, making it unsuitable for many of the heat sensitive systems described herein. Laminar flow cocurrent dryers are advantageously used for heat sensitive materials because inlet gas temperatures up to 305°–310° C. may be used whereas gas and product leave the chamber at 50°–90° C., the material temperature never exceeds the exit gas temperature. Spray dryers are often followed by fluid-bed dryers for second-stage drying and/or cooling.

The inlet temperature at the top of the spray tower should be from about 200° C. to about 275° C. The outlet temperature coming off the tower should be from about 93° C. to about 150° C. Temperatures in excess of these may cause fusing of particles in the agglomerate which is detrimental to spontaneity and redispersion of the water-dispersible granule in water. The temperature of the water-dispersible granule coming out of the tower should be below a temperature at which the shell wall would fuse, e.g., in the case of alachlor about 55°–75° C.

Product coming out of the tower contains 7–9% moisture which requires secondary drying to reduce the moisture to from 2–4%.

In order to obtain an essentially spherical water-dispersible granule (aggregate which is from about 180 to about 420 microns in diameter, it has been found to be advantageous to use a spray-dry tower having an inside diameter and cylindrical drying chambers from about 3.66 to about 12.19 m on with a 60° collection core.

The optimum pressure for operating the spray nozzle is a range of from about 1035–2069×10³ N/m², preferably, from about 1379 to about 2069 and, more preferably, from about 1724 to about 1896×10³ N/m².

The following examples illustrate specific embodiments of the invention. As will be recognized by one skilled in the art, these examples are illustrative and are not meant to be limiting.

Example 1

This example describes the preparation of an aqueous suspension of the microencapsulated alachlor, together with formulation adjuvants.

55.91Kg of technical alachlor maintained at 48° C. containing 3.9 Kg of polymethylene polyphenylisocyanate (PAP I) was metered proportionately to 36.30 Kg of water maintained at 48° C. containing 1.19 Kg of Daxad (40%) emulsifier. An emulsion was formed by passing total mixture through an in-line mixer followed by a Tekmar Dispersator at high shear. To this emulsion 3.90 Kg of HMD was metered proportionately. Encapsulated product passed through second in-line mixer to a tank equipped with adequate agitation. With good agitation add 1.68 Kg propylene glycol. 5.60 Kg NaCl was added, followed with 5.60 Kg CaCl₂ and the mixture stirred.

The aqueous suspension prepared as above, designated herein as "Feedstock No. 1" was then used as the feedstock fed to a spray dryer for removal of water and preparation of water-dispersible (dry-flowable) granules of microencapsulated alachlor as described in Example 2.

Feedstock No. 1 had the following composition:

| INGREDIENT | PERCENT (Wt.) | KILOGRAMS |
| --- | --- | --- |
| Technical Alachlor (94.5%) | 49.00 | 55.91 |

-continued

| INGREDIENT | PERCENT (Wt.) | KILOGRAMS |
|---|---|---|
| PAPI | 3.42 | 3.90 |
| HMD (41%) | 3.43 | 3.90 |
| DAXAD (40%) | 1.04 | 1.19 |
| Proylene Glycol | 1.47 | 1.68 |
| Nacl | 4.90 | 5.60 |
| CaCl₂ | 4.90 | 5.60 |
| Water | 31.85 | 36.30 |
| TOTAL: | 100.00 | 114.08 |

The above feedstock contained 65.6% total solids and had a viscosity of $1300 \times 10^{-3}$ N s/m³.

Example 2

The feedstock prepared in Example 1 was spray dried in accordance with the procedure described below.

The spray tower used in this example had a total height of 9.14 m and diameter of the tower was 6.1 m. The spray dry mode was mix-flow with one pass of feedstock through the tower. The blower speed on this tower was constant, thus, the air flow through the tower was not adjustable. The air inlet temperature was about 245° C. and the air outlet temperature was about 135° C. A Spray Systems single-fluid, hollow-core nozzle was used. The drying volume of the tower was 321.15m³.

The nozzle pressure used was $1896.1 \times 10^3$ N/m².

The particle-size distribution of the water-dispersible granules prepared according to Examples 1 and 2 is set forth in Table 3, together with other product characteristics. Approximately 7% of total dried product was less than 100 mesh. The water-dispersible granules contained about 5% moisture coming from the tower and required secondary drying using a fluid bed dryer/cooler. The final moisture content of the water-dispersible granules was 4% by weight. The water-dispersible granules had excellent spontaneity and dispersion in 10° C. water.

Examples 3-6

Following the same procedure described in Examples 1 and 2, other formulations of microencapsulated alachlor herbicide were prepared as water-dispersible granules. The aqueous suspensions of encapsulated alachlor in Examples 3-6 are designated as Feedstock Nos. 2-5, respectively, and differ from each other in the particular formulation adjuvants used.

The composition of the feedstocks prepared in these examples is set forth in Table 1 and the spray-drying conditions set forth in Table 2. The product characteristic of the water-dispersible granules prepared according to Examples 3-6 are set forth in Table 3.

TABLE 1

FEEDSTOCK FORMULATIONS
(Percent By Weight)

| Ingredients | Feedstock No. 2 | 3 | 4 | 5 |
|---|---|---|---|---|
| Alachlor (94%) | 50.26 | 52.5 | 54.32 | 45.11 |
| Triallate (97.3%) | | | | |
| Acetochlor (93.3%) | | | | |
| Safener AD-67 (94%) | | | | |
| PAPI | 3.55 | 3.7 | 3.79 | 3.14 |
| HMD (41.3 to 43.5%) | 3.55 | 3.6 | 3.76 | 3.21 |
| DAXAD (40%) | | | | |
| Reax 88B | 1.04 | 1.13 | 1.15 | 0.9 |
| Propylene Glycol | | 1.44 | | |
| PVP K-15 | | | | |
| Nacl | 4.28 | 3.39 | 2.55 | |
| Cacl₂ | 4.28 | 3.39 | 3.11 | |
| (NH₄)₂SO₄ | | | | 11.15 |
| Witconate (90) | | | | 4.94 |
| Petro AGS | | | | |
| Duponol C | | | | |
| Hisil 233 | | | | |
| Barden Clay | | | | |
| Water | 33.24 | 30.84 | 32.32 | 31.55 |
| TOTAL: | 100.00 | 100.00 | 100.00 | 100.00 |
| Total Solids | 63.49 | 63.01 | 63.12 | 66.61 |
| Viscosity ($\times 10^{-3}$ N s/m²) | 900 | 925 | 950 | 1200 |

TABLE 2

SPRAY-DRY OPERATING PARAMETERS
Size of Tower - Diameter - 6.71 m; Vertical Ht. - 9.14 m
Drying Volume - 321.15 m³
Nozzles - Multiple: Single-Fluid

| Feedstock No. | 2 | 3 | 4 | 5 | 6 | 7 | 8 | 9 |
|---|---|---|---|---|---|---|---|---|
| Tower Conditions | | | | | | | | |
| Inlet Temp °C. | 232 | 235 | 190 | 230 | 225 | 225 | 225 | 225 |
| Outlet Temp °C. | 125 | 135 | 91 | 125 | 120 | 122 | 120 | 120 |
| Spray Dry Mode* | C-C | C-C | C-C | M-F | M-F | M-F | M-F | M-F |
| Fluidized Bed | | | | | | | | |
| Inlet Temp °C. | 70 | 75 | 80 | 70 | 70 | 70 | 75 | 75 |
| Outlet Temp °C. | 65 | 65 | 70 | 65 | 65 | 65 | 68 | 68 |
| Product Temp °C. | 60 | 65 | 60 | 60 | 55 | 60 | 55 | 58 |
| Rate Kg/Prod/Hr | 371 | 541 | 508 | 574 | 575 | 575 | 680 | 680 |
| Nozzle Pressure ($\times 10^3$ N/m²) | 1551.3 | 1654.8 | 1585.8 | 1896.1 | 1896.1 | 1896.1 | 1723.7 | 1723.7 |

*M-F = Mix Flow; C-C = Co-Current

TABLE 3

PRODUCT CHARACTERISTICS OF WATER-DISPERSIBLE GRANULES

| Feedstock No. | Moisture Off Tower | Moisture Off Fluid Bed | Wetting | Spont | Wet Sieve Residue % On 200 mesh | Granule Size Distribution Cumm. (% on Screen) mesh +40 | +60 | +80 | +100 | <100 | Kg/m³ |
|---|---|---|---|---|---|---|---|---|---|---|---|
| 1 | 5.0 | 2.0 | Ex | Ex | Tr | 20 | 84 | 97 | 99 | 1 | 54.5 |
| 2 | 4.97 | 2.0 | Ex | Ex | Tr | 31 | 88 | 97.6 | 98.9 | 1.1 | 54.5 |
| 3 | 3.9 | 1.40 | Ex | EX | Tr | 39 | 92 | 97.9 | 99.9 | 0.1 | 56.1 |
| 4 | 2.0 | 0.51 | Ex | Ex | 1.0 | 13 | 87 | 97.7 | 99.74 | 0.26 | 54.5 |

TABLE 3-continued

PRODUCT CHARACTERISTICS OF WATER-DISPERSIBLE GRANULES

| Feedstock No. | Moisture Off Tower | Moisture Off Fluid Bed | Wetting | Spont | Wet Sieve Residue % On 200 mesh | Granule Size Distribution Cumm. (% on Screen) mesh +40 | +60 | +80 | +100 | <100 | Kg/m³ |
|---|---|---|---|---|---|---|---|---|---|---|---|
| 5 | 5.0 | 3.04 | VG | VG | 0.1 | 27 | 89 | 99 | 99.8 | 0.2 | 56.1 |
| 6 | 4.0 | 1.0 | Ex | Ex | 0 | 30 | 80 | 95 | 99 | 1 | 44.9 |
| 7 | 1.0 | 0.8 | Ex | Ex | Tr | 62 | 77 | 93 | 98 | 1 | 43.3 |
| 8 | 2.0 | 1.0 | Ex | Ex | 1.0 | 21 | 84 | 97 | 99 | 1 | 51.3 |
| 9 | 2.0 | 0.8 | G | G | 2.0 | 24 | 85 | 97 | 99 | 1 | 51.3 |

G = Good
VG = Very Good
Ex = Excellent
Spont = Spontaniety
Tr = Trace (<0.17%)
Cumm = Cumulative
40 mesh = 420 μm (microns)
60 mesh = 250
80 mesh = 180
100 mesh = 150
2100 mesh = <150

Example 7

This example describes the preparation of an aqueous suspension of microencapsulated triallate and formulation adjuvants therefore.

53.91 Kg of technical triallate maintained at 48° C. containing 3.74 Kg at PAPI was metered proportionately to 35 Kg of water maintained at 48° C. containing 1.37 Kg of DAXAD (40%) emulsifier. Emulsion was formed by passing total mixture through an in-line mixer followed by a Tekmar Dispersator at high shear. To this emulsion 3.26 Kg of HMD (41%) was metered proportionately. Encapsulated product was passed through second in-line mixer to a tank equipped with adequate agitation. With good agitation 1.26 Kg at propylene glycol was added followed by 1.58 Kg NaCl and 3.15 Kg CaCl$_2$.

To this mixture a slurry was added containing 13.6 Kg water, 2.5 Kg PETRO AG-S, 2.5 Kg DUPONOL-C, 1.25 Kg HISILL 233, and 1.25 Kg Barden clay. The mixture was stirred till uniform.

The formulation prepared in accordance with this example had the following composition and is designated as Feedstock No. 6:

| Ingredient | Percent | Kilograms |
|---|---|---|
| Technical Triallate (97.3%) | 43.23 | 53.67 |
| PAPI | 3.02 | 3.74 |
| HMD (41%) | 2.62 | 3.26 |
| DAXAD 16 (40%) | 1.04 | 1.37 |
| Propylene Glycol | 1.01 | 1.26 |
| NaCl | 1.27 | 1.58 |
| CaCl$_2$ | 2.54 | 3.15 |
| Petro AGS | 2.0 | 2.50 |
| DUPONOL C | 2.0 | 2.50 |
| HISIL 233 | 1.0 | 1.25 |
| Barden Clay | 1.0 | 1.25 |
| Water | 39.23 | 48.63 |
| TOTAL: | 100.00 | 124.15 |

Feedstock No. 6, having a solids content of 58.69 wt. % and a viscosity of $1100 \times 10^{-3}$ N s/m², was spray dried under conditions set forth in Table 2 to produce water-dispersible granules of microencapsulated triallate with formulation adjuvants having product characteristics shown in Table 3.

Example 8

Another triallate-based feedstock (Feedstock No. 7) was prepared, but using different formulation adjuvants than those used to prepare Feedstock No. 6. In particular, in the feedstock of this example, REAX 88B (sodium ligno sulfonate) was substituted for DAXAD (sodium salt of polymerized alkyl naphthalene sulfonic acid) as emulsifier and PVP-K-15 (polyvinylpyrrolidone), was substituted for propylene glycol as anti-caking agent.

53.91Kg of technical triallate (97.3%) maintained at 48° C. containing 3.74 Kg at PAPI was metered proportionately to 38 Kg of water maintained at 48° C. containing 1.06 Kg of REAX 88B emulsifier. Emulsion was formed by passing total mixture through an in-line mixer followed by a Tekmar Dispersator at high shear. To this emulsion 3.26 Kg of HMD (41%) was metered proportionately. Encapsulated product passed through a second in-line mixer to a tank equipped with adequate agitation. With good agitation 1.58 Kg NaCl was added followed by 3.15 Kg CaCl$_2$.

To this mixture a slurry was added containing 11.35 Kg water, 0.64 Kg PVP K-15, 2.60K Petro AGS, 2.60 Kg Duponol C, 1.25 Kg HISIL 233, and 1.25 Kg Barden Clay. The mixture was stirred till uniform.

The formulation of Feedstock No. 7 had the following composition:

| Ingredient | Percent | Kilograms |
|---|---|---|
| Technical Triallate (97.3%) | 43.23 | 53.67 |
| PAPI | 3.02 | 3.74 |
| HMD (41%) | 2.62 | 3.26 |
| REAX 88B | 0.84 | 1.06 |
| PVP-K-15 | 0.49 | 0.64 |
| NaCl | 1.27 | 1.58 |
| CaCl$_2$ | 2.54 | 3.15 |
| Petro AGS | 2.10 | 2.60 |
| Duponol C | 2.10 | 2.60 |
| HISIL 233 | 1.00 | 1.25 |
| Barden Clay | 1.00 | 1.25 |
| Water | 39.79 | 49.34 |
| TOTAL: | 100.00 | 124.15 |

Feedstock No. 7 had a total solids content of 58.89% by weight and a viscosity of $1000 \times 10^{-3}$ N s/m². This feedstock was then spray dried under conditions set forth in Table 2 to produce water-dispersible granules having product characteristics shown in Table 3.

Example 9

This example describes the preparation of an aqueous suspension of microencapsulated acetochlor as a feedstock to be dried to produce dry-flowable water-dispersible granules.

55.23 Kg of technical acetochlor (93.3%) containing 3.85 Kg of PAP I was metered proportionately to 37.43 Kg water maintained at 48° C. containing 1.09 Kg REAX 88B emulsifier. An emulsion was formed by passing the mixture through an in-line mixer followed by a Tekmar Dispersator at high shear. To this emulsion 3.35 Kg HMD (41%) was metered. Encapsulated product passed through a second in-line mixer to tank equipped with adequate agitation. With good agitation 10.38 Kg $(NH_4)_2 SO_4$ was added followed by 4.56 Kg Witconate (90), 2.50 Kg HISIL 23, and 1.30 Kg Barden clay. The mixture was stirred until uniform.

The above composition, designated as Feedstock No. 8, had the following composition:

| Ingredient | Percent | Kilograms |
|---|---|---|
| Acetochlor (93.3%) | 46.13 | 55.23 |
| PAPI | 3.20 | 3.85 |
| HMD (41%) | 2.80 | 3.34 |
| REAX 88B | 0.87 | 1.09 |
| $(NH_4)_2 SO_4$ | 8.67 | 10.38 |
| Witconate (90) | 3.81 | 4.56 |
| HISIL 233 | 2.10 | 2.50 |
| Barden Clay | 1.10 | 1.30 |
| Water | 31.32 | 37.44 |
| TOTAL: | 100.00 | 119.6 |

Feedstock No. 8 had a total solids content of 67.29% by weight and a viscosity of $500 \times 10^{-3}$ N s/m². This feedstock was spray-dried according to conditions described in Table 2 to produce water-dispersible granules having product characteristics shown in Table 3.

Example 10

This example describes the preparation of a feedstock (No. 9) containing acetochlor herbicide and a safener therefor, e.g., for use in corn; the safener is N-α,α-dichloroacetyl-1-oxa-4-azaspiro [4,5] decane (common name "AD-67").

To 5.46 Kg of Ad-67 dissolved in 55.23 Kg acetochlor was added 3.85 Kg of PAP I, while maintaining temperature at 48° C. The solution was metered-to 14.07 Kg water maintained at 48° C. containing 1.09 Kg REAX 88B emulsifier. An emulsion was formed by passing through an in-line mixer, followed by a Tekmar Dispersator at high shear. To this emulsion was metered 3.34 Kg HMD (41%). The encapsulated acetochlor-/AD-67 product was passed through a second in-line mixer to a mixing tank equipped with adequate agitation. With good agitation 10.32 Kg $(NH_4)_2 SO_4$ was added followed by a slurry containing 14.07 Kg water, 4.53 Kg Witconate (90), 2.42 Kg HISIL 233, and 1.21 Kg Barden Clay. The mixture was stirred til uniform.

Feedstock No. 9 had the following composition.

| Ingredient | Percent | Kilograms |
|---|---|---|
| Acetochlor (93.3%) | 40.00 | 55.23 |
| AD-67 (94%) | 3.96 | 5.46 |
| PAPI | 2.75 | 3.85 |
| HMD (41%) | 2.41 | 3.34 |
| REAX 88B | 0.75 | 1.09 |
| $(NH_4)_2 SO_4$ | 7.48 | 10.32 |
| Witconate (90) | 3.28 | 4.53 |
| HISIL 233 | 1.76 | 2.42 |
| Barden Clay | 0.88 | 1.21 |
| Water | 36.73 | 50.55 |

-continued

| Ingredient | Percent | Kilograms |
|---|---|---|
| TOTAL: | 100.00 | 138.00 |

Total solids content of the above mixture was 62.11 weight %. Viscosity was $550 \times 10^{-3}$ N s/m².

In similar manner as described in this example, other herbicide/safener combinations may be encapsulated and formed into water-dispersible granules. One particularly suitable combination is a feedstock comprising alachlor herbicide encapsulated together with the safener flurazole, or alternatively, AD-67, within a polymeric shell wall, e.g., a polyurea shell. When said feedstock is spray dried, a dry, free-flowing water-dispersible granule is produced.

Other safeners may similarly be combined with acetochlor, alachlor and other herbicides as discussed earlier herein.

Example 11

The aqueous suspensions of Examples 9 and 10, (Feedstock Nos. 8 and 9, respectively), were then separately spray dried according to the procedure described in Example 2, but-following the operating conditions shown in Table 2 for each feedstock.

Product characteristics for the water-dispersible granules derived from the spray-drying of Feedstocks 8 and 9 are shown (together with those of Feedstock Nos. 1-7) in Table 3.

As will be noted in Table 3, the moisture content of the water-dispersible granules coming off the tower was never more than 5% and off the dried fluid bed dryer was no more than about 3% by weight. For water-dispersible granules derived from Feedstocks 1-9, the particle size retained on 100 mesh sieve was generally 2 microns or less.

As mentioned above, the microencapsulation/ granulation systems herein provide for the presence of formulation additives to aid in these operations to provide the ultimate water-dispersible granule product. Such additives are discussed in more detail below.

In general, the emulsifiers found to be useful in the preparation of the formulations of this invention include ligno sulfonates, alkyl naphthalene sodium sulfonates, e.g., Petro AGS, manufactured by Petro Chemicals Co., Inc., lauryl sulfate, sodium lauryl sulfate, manufactured by E. I. DuPont, α-olefin sulfonates (such as Witconate AOK (90% flake) and Witconate AOS (39% solution), manufactured by Witco Co., taurates, block copolymers of polyethylene/propylene and other surfactants of solid or near-solid consistency.

There are many commercially available salts of lignin sulfonate which may be conveniently employed and many are described in *McCutcheon's Detergents and Emulsifiers,* North American Edition, 1978, McCutcheon Division, McCutcheon Publishing Company, Glen Rock, N.J. Exemplary of such commercially available lignin sulfonates are Treax ® LTS, LTK, and LTM; respectively, the potassium, magnesium, and sodium salts of lignosulfonate, manufactured by Scott Paper Company, Forest Chemical Products; Marasperse CR ® and Marasperse ® CBOS-3, sodium-lignosulfonate, American Can Company, Chemical Products Department, Greenwich, Conn. 06830; Polyfon ® O, H, T, and F and Reax ® 85B and 88B, all of which are sodium lignosulfonates manufactured by Westvaco-Polychemicals, Charleston Heights, S.C. 29405.

Other anionic surfactants which have been found to be useful herein are certain taurate surfactants like sodium N-cyclohexyl-N-palmitoyl taurate, sodium N-methyl-N-oleoyl taurate, respectively, sold under the tradename, Igepon CN-42, Igepon T-33, T-43, T-51, T-73, T-77, and T-74 by GAF Corporation, Chemical Products, New York, N.Y., 10020. Sodium N-methyl-N-oleoyl taurate is also available under the tradename "Adinol" from Croda Chemicals, Ltd., England. Preferred for use herein is sodium N-methyl-N-oleoyl taurate.

The anionic surfactant present in the aqueous suspension of microcapsules prior to spray drying to obtain the formulation of the present invention is from about 0.5 percent to about 5.0 percent by weight of the composition, preferably at from about 1.0 to about 3.5 percent by weight and most preferably at about 2.50 percent by weight. In the formulations of this invention, the anionic surfactant may be used in combination with a nonionic block copolymer.

The nonionic block copolymer surfactants particularly useful in preparing formulations of the present invention are polyoxypropylene/polyoxyethylene block copolymers which are condensates of ethylene oxide with the hydrophobic bases formed by condensing propylene oxide with propylene glycol. Such surfactants have the general formula:

$$HO(CH_2CH_2O)_C(\overset{CH_3}{\underset{|}{C}}HCH_2O)_A(CH_2CH_2O)_BH$$

A is a whole number from about 10 to about 70; B and C are whole numbers, the sum of which will range from about 10 to about 350. Exemplary of such surfactants are Pluronic® P103, P104, P105, and Pluronic F108, which are manufactured by BASF Wyandotte Corporation, Industrial Chemicals Group, Wyandotte, Mich., 48192.

The nonionic block copolymer used in the preparation of the formulations of the present invention at from about 0.75 percent to about 5.0 percent by weight of the composition, preferably at from about 1.25 percent to about 4.0 percent and most preferably at about 1.75 percent by weight of the total formulation.

As used herein, the term "hydrated amorphous silicon dioxide" refers to a finely-divided silica such as naturally occurring Kieselguhr or an artificial silica. Artificial silica is silica which has been produced by a chemical reaction as compared with naturally occurring silica such as Kieselguhr. Preferred for use herein are artificial silicas as, for example, artificial silicas sold under the tradename, "Hi-Sil 233" (manufactured by PPG Industries, Inc., Pittsburgh, Pa., 15222) and "Zeofree 80" (manufactured by J. M. Huber Corporation, Edison, N.J., 08817). There is suitably used at from about 1.0 to about 4.0 percent by weight of the total aqueous composition containing said microcapsules of pesticide dispersed therein, , preferably from about 1.5 to about 3.0 percent by weight and most preferably about 2.0 percent by weight, of silica in the form of water-free or hydrated silica gel or other amorphous silica.

The term "hydrated aluminum silica" as used herein refers to such materials as barden clay or kaolin, which are low surface area materials which have an electrostatic surface charge and thus are able to enhance the stability of the dispersion of microcapsules in the liquid phase. These materials are commercially available from many sources as will be readily recognized by those skilled in the art. The "hydrated aluminum silica" component of the formulation described herein is present at from about. 0.25 to about 3.0 percent by weight, preferably from about 0.25 to about 1.5 percent by weight and most preferably at 0.5 percent by weight of the total composition.

As used herein, the term "flocculent" refers to a suitable salt which contains a polyvalent cation and which is soluble in the amount of water present in the encapsulation composition, which acts to cause the solids in the composition to form small, loosely aggregated bits or particles suspended in the liquid in the composition. Upon spray drying of the liquid composition, these flocculent materials serve to function as binders/separators/anti-caking/detackifying, etc. agents in the water-dispersible granules formulation of the invention. Suitable salts which may be mentioned are $CaCl_2$, $MgCl_2$, $CaBr_2$, $Mg(C_2H_3O_2)_2$, $MgBr_2$, naphthalene salts, Witconate 90, $Al_2(SO_4)_3 \cdot 18H_2O$, $(NH_4)_2SO_4$, $NaNO_3$, and the like, preferred for use herein is $CaCl_2$, Witconate 90 and $(NH_4)_4SO_4$ or combination of the latter two, preferably in ratios above 1:1, especially 1:2.5 (Witconate:$(NH_4)_2SO_4$). The flocculent is present in the composition at from about 0.5 percent to about 5.0 percent by weight, preferably at from about 0.5 to about 2.5 percent by weight and most preferably at 1.00 percent by weight of total composition. As would be recognized by one skilled in the art, the salt will also act to depress the freezing point of the aqueous liquid and thus will act as an antifreeze agent, should one wish to store the liquid suspension of microcapsules prior to spray drying.

Lower alkyl glycols, e.g., ethylene or proplyene glycol, are examples of suitable anti-caking agents useful in the suspension of microcapsules described herein. Amounts of these components ranging from about 2.0 percent to about 10.0 percent by weight of the total composition will adequately provide the composition with the desired anti-caking protection. Suitably, from about 2.0 to about 5.0 percent by weight of the glycol will be present in the formulation, preferably, about 2.5 percent by weight of the anti-caking agent is used in the formulation of the present invention.

Minor quantities, i.e., from 0 to about 5.0 percent by weight of total composition, of one or more other inert formulation adjuvants such as anti-foaming agents, anti-caking agents, biocides, dyes, anti-corrosion agents, acids or bases to adjust pH, and the like, may be incorporated into the liquid suspension of microcapsules prior to spray drying to obtain the water-dispersible granular formulation of the present invention, especially if the liquid suspensions for said formulations are to be stored for any extended period of time prior to spray drying, particularly under adverse storage conditions.

As indicated above, the water-dispersible granules herein may contain up to 75% or more by weight of the active ingredient, the balance being made up of binders/separators/dispersants/anti-caking, etc. formulation additives.

It will be understood by those skilled in the art that some experimentation may be in order to ascertain which of certain suspension adjuvants or agglomeration adjuvants perform most suitably considering the nature of active ingredients and other formulation additives. While, e.g., one emulsifier may tend to enhance caking in storage or reduce spontaneous reconstitution in water, that emulsifier may enhance color stability of the dried granules and, together with other anti-caking agents, serve to provide satisfactory water-dispersible granules.

What is claimed is:

1. Water-dispersible granules comprising:
   (a) an aggregation of essentially spherical microcapsules comprising at least one water-insoluble pesticide encapsulated within a polymeric shell wall,
   (b) formulation adjuvants, and
   (c) up to about 8% by weight moisture, said granules being essentially spherical and having diameters within the range of about 150 to 850 microns.

2. Granules according to claim 1 wherein said microcapsules are from about 1 to about 100 microns in diameter.

3. A free-flowing composition comprising a collection of granules as defined in claim 2.

4. A composition according to claim 3 wherein 90–95% of said granules are from about 180 to about 420 microns in diameter.

5. A composition according to claim 4 wherein said granules are from about 250 to about 420 microns in diameter.

6. A composition according to claim 4 having a bulk density of from about 32 to about 96 kg/m$^3$.

7. A composition according to claim 6 wherein the bulk density is from about 56 to about 72 kg/m$^3$.

8. A composition according to claim 7 wherein said granules contain no more than about 4.0% by weight of moisture.

9. A composition according to claim 8 wherein said granules contain from about 1.0% to about 2.0% by weight of moisture.

10. A composition according to claim 9 wherein said microcapsules are from about 1 to about 50 microns in diameter.

11. Composition according to claim 3 wherein said granules contain an effective amount of said pesticide up to 90% by weight.

12. Composition according to claim 11 wherein said pesticide is a herbicide.

13. Composition according to claim 12 wherein said herbicide is alachlor.

14. Composition according to claim 12 wherein said herbicide is triallate.

15. Composition according to claim 12 wherein said herbicide is acetochlor.

16. Composition according to claim 12 wherein said microcapsules contain a safener for said herbicides.

17. Composition according to claim 16 wherein said herbicide is acetochlor and said safener is AD-67.

18. Composition according to claim 16 wherein said herbicide is alachlor and said safener is flurazole.

19. A process for preparing water-dispersible granules comprising:
   (a) forming an aqueous suspension comprising discrete microcapsules containing at least one water-insoluble pesticide within a polymeric shell wall suspended in an aqueous medium and formulation adjuvants, and
   (b) forming droplets of said aqueous suspension and spray drying said droplets to form water-dispersible granules as defined in claim 1.

20. A process according to claim 19 wherein said water-insoluble pesticide is a herbicide.

21. A process according to claim 20 wherein said herbicide is alachlor.

22. A process according to claim 20 wherein said herbicide is triallate.

23. A process according to claim 20 wherein said herbicide is acetochlor.

24. A process according to claim 19 wherein said water-dispersible granules are from about 180 to about 420 microns in diameter.

25. A process according to claim 24 wherein said water-dispersible granules are from about 250 to about 450 microns in diameter.

26. A process according to claim 24 wherein said water-dispersible granules have a bulk density of from about 32 to about 96 kg/m$^3$.

27. A process according to claim 26 wherein the bulk density of said water-dispersible granules is from about 56 to about 72 kg/m$^3$.

28. A process according to claim 26 wherein said water-dispersible granules contain no more than about 4.0% by weight of moisture.

29. A process according to claim 28 wherein said water-dispersible granules contain from about 1.0% to about 2.0% by weight of moisture.

30. A process according to claim 19 wherein said individual, spherical microcapsules are from about 1 to about 100 microns in diameter.

31. A process according to claim 30 wherein said individual, spherical microcapsules are from about 1 to about 50 microns in diameter.

32. Process according to claim 20 wherein said microcapsules contain a safener for said herbicide.

33. Process according to claim 32 wherein said herbicide is acetochlor and said safener is AD-67.

34. Process according to claim 32 wherein said herbicide is alachlor and said safener is flurazole.

* * * * *